US012702340B2

(12) United States Patent
Koo et al.

(10) Patent No.: US 12,702,340 B2
(45) Date of Patent: Aug. 11, 2026

(54) METHOD AND APPARATUS WITH NEURAL RECORDING

(71) Applicant: SAMSUNG ELECTRONICS CO., LTD., Suwon-si (KR)

(72) Inventors: Nahm il Koo, Suwon-si (KR); Chisung Bae, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 734 days.

(21) Appl. No.: 18/112,705

(22) Filed: Feb. 22, 2023

(65) Prior Publication Data

US 2024/0057920 A1 Feb. 22, 2024

(30) Foreign Application Priority Data

Aug. 17, 2022 (KR) ........................ 10-2022-0102755

(51) Int. Cl.
*A61B 5/304* (2021.01)
*A61B 5/311* (2021.01)

(52) U.S. Cl.
CPC .............. *A61B 5/304* (2021.01); *A61B 5/311* (2021.01)

(58) Field of Classification Search
CPC ......... A61B 5/7225; A61B 5/30; A61B 5/053; A61B 5/24; A61B 5/7203; A61B 5/369; A61B 5/01; A61B 5/7228; A61B 2560/0219; A61B 5/0031; A61B 5/291; A61B 5/14546; A61B 8/4494; A61B 8/4488; A61B 5/6868; A61B 5/036; A61B 5/14532; A61B 8/488; A61B 8/5207; A61B 2562/0247; A61B 5/0006; A61B 5/293; A61B 2562/0219; A61B 8/4483; A61B 5/14552; A61B 5/4094; A61B 5/14539;

(Continued)

(56) References Cited

U.S. PATENT DOCUMENTS

| | | | | |
|---|---|---|---|---|
| 10,702,183 | B2 | 7/2020 | Harrison | |
| 11,607,549 | B2 * | 3/2023 | Marnfeldt | A61N 1/08 |

(Continued)

FOREIGN PATENT DOCUMENTS

| | | | | |
|---|---|---|---|---|
| CA | 2453146 | * | 1/2003 | H04L 25/02 |
| EP | 3 780 394 | A1 | 2/2021 | |
| KR | 10-1970692 | B1 | 4/2019 | |

OTHER PUBLICATIONS

Abbott et al. "A nanoelectrode array for obtaining intracellular recordings from thousands of connected neurons" *Nature biomedical engineering* vol. 4 No. 2, Sep. 23, 2019 (pp. 1-26).

(Continued)

*Primary Examiner* — John W Poos
(74) *Attorney, Agent, or Firm* — NSIP Law

(57) ABSTRACT

A neural recording apparatus including an electrode array including a plurality of electrodes configured to detect voltage signals of one or more neurons and a reference electrode configured to detect a reference signal, a regulator configured to regulate the reference signal, a plurality of transconductance circuits configured to generate current signals by performing transconductance based on the voltage signals and the regulated reference signal, a multiplexer (MUX) configured to multiplex on the generated current signals, and an analog-to-digital converter (ADC) configured to convert the multiplexed current signals into a digital signal.

20 Claims, 11 Drawing Sheets

(58) Field of Classification Search

CPC ... A61B 5/7275; A61B 5/6833; A61B 8/4427; A61B 2560/0468; A61B 2562/043; A61B 2562/046; A61B 5/31; A61B 5/316; A61B 5/4082; A61B 5/686; A61B 8/56; A61B 5/0024; A61B 5/318; A61B 8/0883; A61B 2560/0214; A61B 2560/0412; A61B 2562/164; A61B 5/389; A61B 5/6853; A61B 5/742; A61B 5/7475; A61B 2560/0443; A61B 2562/063; A61B 5/0084; A61B 5/0537; A61B 5/4836; A61B 5/725; A61B 5/021; A61B 5/486; A61B 8/4472; A61B 8/54; A61B 5/14503; A61B 5/374; A61B 5/4851; A61B 8/483; A61B 8/546; A61B 2560/0209; A61B 5/00; A61B 5/0205; A61B 5/7278; A61B 8/145; A61B 17/74; A61B 17/80; A61B 2560/0431; A61B 2562/125; A61B 2562/166; A61B 5/0002; A61B 5/02014; A61B 5/02055; A61B 5/02108; A61B 5/026; A61B 5/029; A61B 5/6812; A61B 5/6862; A61B 5/7242; A61B 2018/00839; A61B 2562/0233; A61B 5/305; A61B 5/7221; A61B 8/14; A61B 2562/04; A61B 5/0071; A61B 5/14551; A61B 5/14553; A61B 5/1495; A61B 5/304; A61B 5/6843; A61B 5/6861; A61B 5/7217; A61B 5/7232; A61B 5/7235; A61B 5/7267; A61B 8/4444; A61B 2017/0023; A61B 2562/0223; A61B 2562/0238; A61B 2562/14; A61B 5/0028; A61B 5/0036; A61B 5/0531; A61B 5/073; A61B 5/103; A61B 5/339; A61B 5/4255; A61B 5/4519; A61B 5/6832; A61B 5/684; A61B 5/7405; A61B 8/13; A61B 8/4411; A61B 8/4477; A61B 8/461; A61B 10/0038; A61B 10/0045; A61B 2010/0061; A61B 2010/0074; A61B 2560/0252; A61B 5/0022; A61B 5/02427; A61B 5/11; A61B 5/282; A61B 5/42; A61B 5/4238; A61B 5/6803; A61B 5/6898; A61B 6/037; A61B 5/0075; A61B 5/0538; A61B 5/308; A61B 5/4064; A61B 2562/0261; A61B 3/1015; A61B 3/102; A61B 3/122; A61B 5/375; A61B 5/7257; A61B 8/06; A61B 8/587; A61B 18/1492; A61B 2018/00577; A61B 3/0025; A61B 3/1035; A61B 3/113; A61B 3/132; A61B 3/14; A61B 3/152; A61B 5/6814; A61B 5/7264; A61B 2560/0406; A61B 2562/0209; A61B 2562/0285; A61B 5/024; A61B 5/02416; A61B 5/0261; A61B 5/1101; A61B 5/1112; A61B 5/117; A61B 5/145; A61B 5/262; A61B 5/283; A61B 5/332; A61B 5/333; A61B 5/346; A61B 5/352; A61B 5/361; A61B 5/6885; A61B 5/7207; A61B 5/7253; A61B 5/726; A61B 8/58; A61B 18/02; A61B 18/20; A61B 2018/0016; A61B 2018/0022; A61B 2018/00357; A61B 2018/00648; A61B 2018/00875; A61B 2018/0212; A61B 2018/0237; A61B 2018/0262; A61B 2560/0475; A61B 2562/0215; A61B 5/0017; A61B 5/0215; A61B 5/02405; A61B 5/05; A61B 5/08; A61B 5/1455; A61B 5/1459; A61B 5/1473; A61B 5/259; A61B 5/287; A61B 5/377; A61B 5/383; A61B 5/398; A61B 5/681; A61B 2017/00084; A61B 2562/0204; A61B 2562/028; A61B 5/0077; A61B 5/0095; A61B 5/0536; A61B 5/076; A61B 5/257; A61B 5/28; A61B 5/355; A61B 5/358; A61B 5/37; A61B 5/4818; A61B 5/4839; A61B 5/4845; A61B 5/4875; A61B 5/6831; A61B 5/6848; A61B 5/685; A61B 5/7239; A61B 7/003; A61B 7/04; A61B 8/08; A61B 8/0891; A61B 8/46; A61B 1/04; A61B 17/3403; A61B 17/3468; A61B 2017/00367; A61B 2034/2057; A61B 2560/0257; A61B 2562/0242; A61B 34/20; A61B 5/0051; A61B 5/02141; A61B 5/02438; A61B 5/0535; A61B 5/14865; A61B 5/277; A61B 5/302; A61B 5/4041; A61B 5/412; A61B 5/415; A61B 5/418; A61B 5/6823; A61B 5/6824; A61B 5/6888; A61B 6/032; A61B 6/4258; A61B 6/508; A61B 8/469; A61B 18/00; A61B 18/04; A61B 2018/00404; A61B 2018/00434; A61B 2018/00511; A61B 2018/00702; A61B 2018/00833; A61B 2018/00845; A61B 2503/04; A61B 2503/06; A61B 2503/10; A61B 2560/0276; A61B 34/30; A61B 34/73; A61B 5/0004; A61B 5/0042; A61B 5/0059; A61B 5/022; A61B 5/037; A61B 5/121; A61B 5/14507; A61B 5/1468; A61B 5/14735; A61B 5/1477; A61B 5/201; A61B 5/204; A61B 5/207; A61B 5/208; A61B 5/25; A61B 5/296; A61B 5/311; A61B 5/366; A61B 5/372; A61B 5/388; A61B 5/4088; A61B 5/413; A61B 5/4812; A61B 5/6804; A61B 5/6808; A61B 5/6826; A61B 5/6846; A61B 5/7214; A61B 5/7455; A61B 5/746; A61B 6/425; A61B 6/482; A61B 8/00; A61B 8/065; A61B 8/42; A61B 8/4263; A61B 8/463; A61B 8/48; A61B 8/5223; A61B 8/565; A61B 1/00135; A61B 1/00158; A61B 1/041; A61B 2560/04; A61B 2560/0462; A61B 2562/0214; A61B 2562/0252; A61B 2562/162; A61B 2562/227; A61B 5/0015; A61B 5/002; A61B 5/0044; A61B 5/02125; A61B 5/0532; A61B 5/055; A61B 5/062; A61B 5/112; A61B 5/14556; A61B 5/245; A61B 5/273; A61B 5/276; A61B 5/294; A61B 5/307; A61B 5/313; A61B 5/384; A61B 5/4023; A61B 5/4854; A61B 5/4866; A61B 5/4872; A61B 5/6807; A61B 5/682; A61B 5/6838; A61B 6/00; A61B 6/4423; A61B 8/4281; A61B 8/467; G06N 3/063; G01R 31/28; H03M 1/1225; H03M 1/14; H03M 1/46; H03M 3/39; H03M 3/398; H03M 3/422; H03M 3/46; H03M 3/462; H03M 3/47; H03M 3/474; H03M 1/12; H03M 3/458; H03M 1/002; H03M 1/1009; H03M 3/424; H03M 1/121; H03M 3/464; H03M 1/662; H03M 1/124; H03M 1/56; H03M 3/344; H03M

1/0836; H03M 3/468; H03M 1/1057; H03M 1/0845; H03M 1/123; H03M 1/68; H03M 1/682; H03M 1/0614; H03M 1/34; H03M 1/00; H03M 1/007; H03M 1/1028; H03M 1/1205; H03M 3/38; H03M 1/0607; H03M 1/126; H03M 1/18; H03M 1/1019; H03M 1/747; H03M 1/1038; H03M 1/361; H03M 1/0673; H03M 1/1061; H03M 1/808; H03M 3/338; H03M 3/414; H03M 1/0641; H03M 1/664; H03M 1/1014; H03M 1/122; H03M 1/442; H03M 3/402; H03M 3/494; H03M 3/496; H03M 1/0863; H03M 3/322; H03M 3/358; H03M 1/0602; H03M 1/0604; H03M 1/204; H03M 1/50; H03M 1/0678; H03M 1/0682; H03M 3/384; H03M 3/40; H03M 3/45; H03M 3/466; H03M 1/089; H03M 1/508; H03M 1/76; H03M 3/49; H03M 1/005; H03M 1/0665; H03M 1/0692; H03M 1/1235; H03M 1/1255; H03M 1/188; H03M 1/40; H03M 1/785; H03M 1/804; H03M 3/404; H03M 3/426; H03M 3/48; H03M 5/02; H03M 1/10; H03M 1/181; H03M 13/47; H03M 13/6597; H03M 3/392; H03M 3/394; H03M 9/00; H03M 1/0612; H03M 1/0643; H03M 1/0646; H03M 1/0818; H03M 1/0827; H03M 1/1245; H03M 1/365; H03M 1/1215; H03M 1/66; H03M 1/009; H03M 3/454; H03M 1/38; H03M 3/43; H03M 1/0626; H03M 1/462; H03M 1/742; H03M 1/183; H03M 1/1071; H03M 1/1023; H03M 1/502; H03M 3/408; H03M 1/164; H03M 1/468; H03M 1/765; H03M 3/476; H03M 1/466; H03M 3/32; H03M 1/74; H03M 1/745; H03M 1/145; H03M 1/60; H03M 1/08; H03M 1/0881; H03M 3/436; H03M 3/502; H03M 3/34; H03M 1/0609; H03M 3/37; H03M 1/1295; H03M 1/661; H03M 3/386; H03M 3/396; H03M 3/452; H03M 3/438; H03M 3/50; H03M 1/162; H03M 1/167; H03M 3/456; H03M 1/001; H03M 1/0668; H03M 1/201; H03M 3/30; H03M 7/3059; H03M 7/3062; H03M 1/0639; H03M 1/1033; H03M 7/30; H03M 1/0624; H03M 1/16; H03M 1/82; H03M 3/41; H03M 3/412; H03M 1/004; H03M 1/0617; H03M 1/186; H03M 1/363; H03M 3/352; H03M 3/42; H03M 1/06; H03M 1/066; H03M 1/0854; H03M 1/1004; H03M 1/129; H03M 1/141; H03M 1/447; H03M 1/687; H03M 3/356; H03M 3/388; H03M 3/472; H03M 7/3026; H03M 7/3033; H03M 1/362; H03M 1/504; H03M 3/368; H03M 3/382; H03M 3/434; H03M 3/484; H03M 1/0629; H03M 1/068; H03M 1/0695; H03M 1/1042; H03M 1/1047; H03M 1/125; H03M 1/165; H03M 1/168; H03M 1/182; H03M 1/245; H03M 1/366; H03M 1/367; H03M 1/685; H03M 1/86; H03M 13/015; H03M 13/05; H03M 13/09; H03M 13/1102; H03M 13/1111; H03M 13/1171; H03M 13/15; H03M 13/255; H03M 13/27; H03M 13/45; H03M 13/6306; H03M 3/342; H03M 3/346; H03M 3/366; H03M 3/372; H03M 3/378; H03M 3/448; H03M 3/478; H03M 3/488; H03M 3/492; H03M 3/498; H03M 3/51; H03M 7/3022; H03M 1/0619; H03M 1/0872; H03M 1/44; H03M 1/464; H03M 1/70; H03M 1/80; H03M 1/822; H03M 13/11; H03M 3/022; H03M 3/328; H03M 3/362; H03M 3/364; H03M 3/374; H03M 3/444; H03M 3/508; H03M 7/3013; H03M 7/3082; H03L 7/099; H03L 7/0995; H03L 7/18; H03L 7/091; H03L 7/07; H03L 2207/50; H03L 7/0814; H03L 7/0816; H03L 7/148; H03L 7/093; H03L 7/0805; H03L 7/08; H03L 7/087; H03L 7/1976; H03L 1/022; H03L 3/00; H03L 7/085; H03L 7/0812; H03L 7/1974; H03L 2207/06; H03L 7/00; H03L 7/0992; H03L 7/24; H03L 7/0891; H03L 7/0991; H03L 7/0807; H03L 7/14; H03L 1/00; H03L 7/081; H03L 7/06; H03L 7/183; H03L 5/00; H03L 7/083; H03L 7/10; H03L 2207/12; H03L 7/0802; H03L 7/104; H03L 1/023; H03L 1/026; H03L 7/089; H03L 7/185; H03L 7/1806; H03L 7/23; H03L 7/16; H03L 7/095; H03L 7/107; H03L 1/02; H03L 1/025; H03L 7/1075; H03L 7/187; H03L 7/0893; H03L 7/0898; H03L 7/0998; H03L 7/1072; H03L 7/113; H03L 7/189; H03L 7/193; H03L 7/22; H03L 2207/00; H03L 7/02; H03L 7/0895; H03L 7/097; H03L 7/0994; H03L 7/0997; H03L 7/102; H03L 7/105; H03L 7/1077; H03L 7/1803; H03L 7/191; H03L 1/028; H03K 5/2481; H03K 5/131; H03K 5/135; H03K 5/1565; H03K 19/018585; H03K 5/14; H03K 5/249; H03K 2005/00058; H03K 3/0315; H03K 2005/00039; H03K 19/00384; H03K 2217/0027; H03K 17/0822; H03K 17/18; H03K 5/24; H03K 7/08; H03K 17/00; H03K 17/005; H03K 3/017; H03K 7/06; H03K 19/20; H03K 2017/0806; H03K 3/012; H03K 5/003; H03K 17/162; H03K 17/955; H03K 19/017509; H03K 19/17728; H03K 19/1776; H03K 2005/00019; H03K 3/037; H03K 5/00006; H03K 17/9622; H03K 19/018528; H03K 19/17736; H03K 19/1778; H03K 19/17796; H03K 3/0231; H03K 17/145; H03K 3/0322; H03K 5/13; H03K 5/133; H03K 17/08142; H03K 5/1252; H03K 5/2472; H03K 17/223; H03K 19/017581; H03K 2005/00052; H03K 5/15; H03K 5/1502; H03K 17/08122; H03K 17/6872; H03K 19/0005; H03K 19/018521; H03K 19/018571; H03K 2005/00071; H03K 2005/00286; H03K 5/01; H03K 5/023; H03K 17/693; H03K 19/00346; H03K 19/1737; H03K 19/21; H03K 2005/00026; H03K 2005/00065; H03K 2217/0036; H03K 2217/960725; H03K 3/356139; H03K 5/04; H03K 5/134; H03K 5/1532; H03K 17/0828; H03K

17/164; H03K 17/687; H03K 17/6871; H03K 19/0008; H03K 19/0013; H03K 19/0027; H03K 19/00369; H03K 19/09432; H03K 19/173; H03K 19/195; H03K 19/1958; H03K 2005/00078; H03K 2017/6875; H03K 21/02; H03K 2217/94031; H03K 2217/96058; H03K 2217/960705; H03K 23/66; H03K 23/662; H03K 3/0375; H03K 3/356069; H03K 3/356147; H03K 5/06; H03K 5/1515; H03K 17/0416; H03K 17/962; H03K 19/0185; H03K 19/17756; H03K 2005/00084; H03K 2005/00247; H03K 2217/0018; H03K 3/356104; H03K 3/356191; H03K 5/05; H03K 5/15066; H03K 5/159; H03K 5/22; H03K 17/04123; H03K 17/122; H03K 17/14; H03K 17/165; H03K 17/625; H03K 17/6264; H03K 17/795; H03K 17/92; H03K 19/0016; H03K 19/003; H03K 19/017527; H03K 19/017545; H03K 19/018507; H03K 19/094; H03K 19/09407; H03K 19/09429; H03K 19/09441; H03K 19/17732; H03K 19/17764; H03K 19/17768; H03K 19/185; H03K 2005/0045; H03K 2005/00097; H03K 2005/00195; H03K 21/08; H03K 2217/0009; H03K 2217/960775; H03K 23/507; H03K 3/01; H03K 3/011; H03K 3/356; H03K 3/356026; H03K 4/00; H03K 4/023; H03K 4/08; H03K 5/00; H03K 5/02; H03K 5/08; H03K 5/12; H03K 5/15026; H03K 5/1534; H03K 17/04106; H03K 17/063; H03K 17/08104; H03K 17/08116; H03K 17/12; H03K 17/167; H03K 17/284; H03K 17/302; H03K 17/56; H03K 17/64; H03K 17/689; H03K 17/722; H03K 17/723; H03K 17/735; H03K 17/941; H03K 17/9631; H03K 19/00315; H03K 19/00361; H03K 19/00376; H03K 19/0136; H03K 19/01837; H03K 19/018578; H03K 19/018592; H03K 19/17744; H03K 19/215; H03K 2005/00104; H03K 2005/00176; H03K 2005/00254; H03K 2005/0026; H03K 2017/6878; H03K 21/026; H03K 21/10; H03K 21/38; H03K 2217/0063; H03K 2217/0072; H03K 2217/94026; H03K 23/544; H03K 23/68; H03K 3/2821; H03K 3/2885; H03K 3/356121; H03K 3/78; H03K 5/082; H03K 5/084; H03K 5/15013; H03K 5/1506

See application file for complete search history.

(56) References Cited

U.S. PATENT DOCUMENTS

| | | | | |
|---|---|---|---|---|
| 2005/0090756 | A1* | 4/2005 | Wolf | A61B 5/30 607/48 |
| 2013/0310897 | A1* | 11/2013 | Marnfeldt | A61N 1/36153 607/62 |
| 2016/0017268 | A1 | 1/2016 | Kim et al. | |
| 2020/0178823 | A1 | 6/2020 | Lu et al. | |
| 2021/0194495 | A1* | 6/2021 | Ballini | H03M 1/46 |
| 2022/0052641 | A1 | 2/2022 | Chien et al. | |

OTHER PUBLICATIONS

Abbott et al. "The Design of a CMOS Nanoelectrode Array with 4096 Current-Clamp/Voltage-Clamp Amplifiers for Intracellular Recording/Stimulation of Mammalian Neurons" *IEEE journal of solid-state circuits* vol. 55 No. 9, Sep. 1, 2020 (pp. 1-43).

Yuan et al. "Extracellular Recording of Entire Neural Networks Using a Dual-Mode Microelectrode Array With 19584 Electrodes and High SNR" *IEEE journal of solid-state circuits* vol. 56 No. 8, Aug. 1, 2021 (pp. 1-24).

Kim et al. "Frequency-Division Multiplexing with Graphene Active Electrodes for Neurosensor Applications" *IEEE Transactions on Circuits and Systems II: Express Briefs* vol. 68 No. 5, May 1, 2021 (pp. 1-16).

* cited by examiner

METHOD AND APPARATUS WITH NEURAL RECORDING

CROSS-REFERENCE TO RELATED APPLICATIONS

This application claims the benefit under 35 USC § 119(a) of Korean Patent Application No. 10-2022-0102755, filed on Aug. 17, 2022, in the Korean Intellectual Property Office, the entire disclosure of which is incorporated herein by reference for all purposes.

BACKGROUND

1. Field

The following description relates to a method and apparatus for neural recording.

2. Description of Related Art

Typical analog front-end (AFE) circuits may include an instrumentation amplifier (IA) and an analog-to-digital converter (ADC) corresponding to each of the electrodes. Such AFE circuits may amplify a measured electrical signal of electrodes, e.g., of a microelectrode array, through the corresponding IA and may convert the amplified electrical signal into a digital signal through the corresponding ADC.

SUMMARY

In one general aspect, a neural recording apparatus includes a plurality of electrodes, the plurality of electrodes being configured to respectively detect voltage signals of one or more neurons and a reference electrode configured to detect a reference signal of a neuron, a regulator configured to regulate the reference signal, transconductance circuits configured to generate respective current signals by performing transconductance based on multiple voltage signals, of the detected voltage signals, and the regulated reference signal, a first multiplexer (MUX) configured to multiplex the current signals, and an analog-to-digital converter (ADC) configured to convert the multiplexed current signals into a digital signal, each of the transconductance circuits including a transistor configured to perform the transconductance and a capacitor connected to the transistor, the regulator being configured to apply the regulated reference signal to the transistor of each of the transconductance circuits as a source voltage.

Each of the transconductance circuits may include a bias resistance connected to a respective gate of the transistor of each of the transconductance circuits and to one end of the capacitor of each of the transconductance circuits.

Each of the transconductance circuits may be configured to receive each of the detected voltage signals, and the capacitor of each of the transconductance circuits may be configured to remove a direct current (DC) component of a respectively received voltage signal.

Each of the voltage signals from which the DC component is removed and each of bias signals may be configured to be applied as a gate voltage of the transistor of each of the transconductance circuits.

The apparatus may include a control circuit configured to merge current signals corresponding to a same neuron among the current signals.

The control circuit may be configured to control the first MUX so that the current signals corresponding to the same neuron are simultaneously output from the first MUX.

The apparatus may also include a first voltage source configured to generate a first voltage signal in a test mode for performing calibration and configured not to generate the first voltage signal in a measurement mode for detecting the voltage signals and a second voltage source configured to generate a test voltage signal in the test mode and configured not to generate the test voltage signal in the measurement mode.

The regulator may include an operational amplifier and a second MUX connected to an input terminal of the operational amplifier, the second MUX being configured to transmit the first voltage signal to the operational amplifier in the test mode and configured to transmit the reference signal to the operational amplifier in the measurement mode. Each of the transconductance circuits further may include a third MUX, the third MUX being configured to transmit the test voltage signal to the capacitor of each of the transconductance circuits in the test mode and configured to transmit each of the detected voltage signals to the capacitor of each of the transconductance circuits in the measurement mode.

The regulator, the plurality of transconductance circuits, the MUX, and the ADC of the apparatus my form an analog front-end (AFE) circuit.

The apparatus may also include a communication circuit configured to transmit the digital signal to an external device.

In a general aspect, a neural recording apparatus includes an electrode array that includes electrodes configured to respectively detect voltage signals of one or more neurons and a reference electrode configured to detect a reference signal, a regulator configured to regulate the detected reference signal as a regulated signal, transconductance circuits configured to generate current signals by performing transconductance based on the voltage signals and the regulated signal, an analog-to-digital converter (ADC), a plurality of switches positioned between the transconductance circuits and the ADC, and a control circuit configured to turn on a switch of each of the transconductance circuits that generates the current signals corresponding to a same neuron among the plurality of switches so that current signals corresponding to the same neuron among the current signals are merged and input to the ADC, and each of the transconductance circuits includes a transistor configured to perform the transconductance and a capacitor connected to the transistor, and the regulator is configured to apply the regulated signal to the transistor of each of the transconductance circuits as a source voltage.

The control circuit may be configured to turn on first switches among the plurality of switches so that first current signals corresponding to a first neuron among the current signals are merged and input to the ADC while turning off second switches, the second switches comprising a first remaining portion of the plurality of switches excluding the first switches and turn on third switches among the plurality of switches so that second current signals corresponding to a second neuron among the current signals are merged and input to the ADC while turning off fourth switches, the fourth switches comprising a second remaining portion of the plurality of switches excluding for the third switches.

Each of the transconductance circuits further may include a bias resistance connected to a respective gate of the transistor of each of the transconductance circuits and one end of the capacitor of each of the transconductance circuits.

Each of the transconductance circuits may be configured to receive each of the voltage signals, and the capacitor of each of the transconductance circuits may be configured to remove a direct current (DC) component of a respectively received voltage signal.

Each of the voltage signals from which the DC component is removed and each of bias signals may be configured to be applied as a gate voltage of the transistor of each of the transconductance circuits.

The neural recording apparatus may also include a first voltage source configured to generate a first voltage signal in a test mode for performing calibration and configured not to generate the first voltage signal in a measurement mode for detecting the voltage signals, and a second voltage source configured to generate a test voltage signal in the test mode and configured not to generate the test voltage signal in the measurement mode.

The regulator may also include an operational amplifier and a MUX connected to an input terminal of the operational amplifier and configured to transmit the first voltage signal to the operational amplifier in the test mode and configured to transmit the reference signal to the operational amplifier in the measurement mode. Each of the transconductance circuits may also include a second MUX configured to transmit the test voltage signal to the capacitor of each of the transconductance circuits in the test mode and configured to transmit each of the voltage signals to the capacitor of each of the transconductance circuits in the measurement mode.

The regulator, the plurality of transconductance circuits, the ADC, the plurality of switches, and the control circuit of the neural recording apparatus may form an analog front-end (AFE) circuit.

In a general aspect, a method includes detecting voltage signals of one or more neurons and a reference signal of a neuron through an electrode array, generating current signals by performing respective transconductances on the detected voltage signals, each transconductance being based on the reference signal, performing multiplexing on the current signals through a multiplexer (MUX), and converting the multiplexed current signals into a digital signal through an analog-to-digital converter (ADC).

The method may also include merging current signals corresponding to a same neuron among the generated current signals.

The method may also include regulating the reference signal through a regulator. Each of plural transconductance circuits, respectively performing the transconductances, may include a transistor configured to perform a corresponding transconductance, and a capacitor connected to the transistor to respectively remove a corresponding DC voltage from a corresponding detected voltage signal applied to the capacitor, and the regulator may be configured to apply the regulated reference signal to the transistor of each of the transconductance circuits as a source voltage.

Other features and aspects will be apparent from the following detailed description, the drawings, and the claims.

Figure 1:
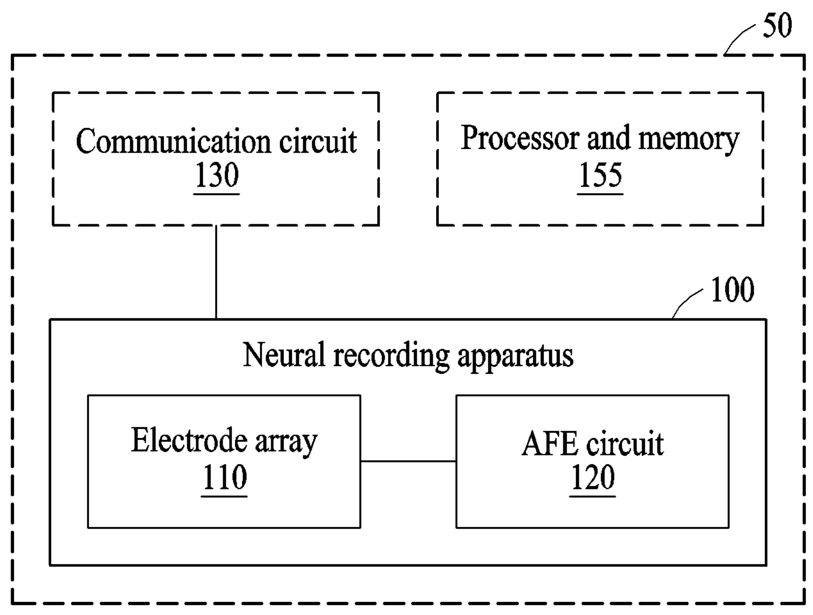
FIG. 1 illustrates an example of a neural recording apparatus according to one or more embodiments.

Throughout the drawings and the detailed description, unless otherwise described or provided, the same or like drawing reference numerals may be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of the disclosure of this application. For example, the sequences of operations described herein are merely examples, and are not limited to those set forth herein, but may be changed as will be apparent after an understanding of the disclosure of this application, with the exception of operations necessarily occurring in a certain order.

The features described herein may be embodied in different forms and are not to be construed as being limited to the examples described herein. Rather, the examples described herein have been provided merely to illustrate some of the many possible ways of implementing the methods, apparatuses, and/or systems described herein that will be apparent after an understanding of the disclosure of this application.

Advantages and features of the present disclosure and methods of achieving the advantages and features will be clear with reference to embodiments described in detail below together with the accompanying drawings. However, the present disclosure is not limited to the embodiments disclosed herein but will be implemented in various forms. The embodiments of the present disclosure are provided so that the present disclosure is disclosed, and a person with ordinary skill in the art can understand the scope of the present disclosure. Meanwhile, the terms used in the present specification are for explaining the embodiments, not for limiting the present disclosure. The use of the term "may" herein with respect to an example or embodiment (for example, as to what an example or embodiment may include or implement) means that at least one example or embodiment exists where such a feature is included or implemented, while all examples are not limited thereto.

Terms, such as first, second, A, B, (a), (b) or the like, may be used herein to describe components. Each of these terminologies is not used to define an essence, order or sequence of a corresponding component but used merely to distinguish the corresponding component from other component(s). For example, a first component may be referred to as a second component, and similarly the second component may also be referred to as the first component.

Throughout the specification, when a component is described as being "connected to," or "coupled to" another component, it may be directly "connected to," or "coupled to" the other component, or there may be one or more other components intervening therebetween. In contrast, when an element is described as being "directly connected to," or "directly coupled to" another element, there can be no other elements intervening therebetween.

In a description of the embodiment, in a case in which any one element is described as being formed on or under another element, such a description includes both a case in which the two elements are formed in direct contact with each other and a case in which the two elements are in indirect contact with each other with one or more other elements interposed between the two elements. In addition, when one element is described as being formed on or under another element, such a description may include a case in which the one element is formed at an upper side or a lower side with respect to another element.

The singular forms "a", "an", and "the" are intended to include the plural forms as well, unless the context clearly indicates otherwise. It will be further understood that the terms "comprises/comprising" and/or "includes/including" when used herein, specify the presence of stated features, integers, steps, operations, elements, and/or components, but do not preclude the presence or addition of one or more other features, integers, steps, operations, elements, components and/or groups thereof.

FIG. 1 illustrates an example of a neural recording apparatus.

Referring to FIG. 1, a neural sensing system 50 includes a neural recording apparatus 100 may include an electrode array 110 and an analog front-end (AFE) circuit 120. The neural sensing system may further include a communication circuit 130 in communication with the neural recording apparatus, and a processor and memory 155 which may communicate with the communication circuit 130.

The neural recording apparatus 100 may be implemented as a chip.

The electrode array 110 may correspond to a microelectrode array (MEA).

The electrode array 110 may include a plurality of electrodes. For example, the electrodes may be spaced apart by a 20 micrometer (μm) pitch.

Each of the electrodes of the electrode array 110 may be configured to detect or obtain an electrical signal (e.g., a voltage signal) generated from a target. The target may include neural targets such as a neuron, a brain cell, or a brain nerve cell that are in contact with each of one or more electrodes, and which generate respective voltages in response to a stimulation, e.g., from other target(s) and/or from the respective electrodes of the electrode array 110. For example, the neural recording apparatus 100 may stimulate the target of each of the electrodes by applying respective electrical signals to the target using the one or more electrodes of the electrode array 110. The applied electrical signals may respectively be one of a voltage signal or a current signal. When the target of each of the electrodes is stimulated by the applied electrical signal, a voltage signal may be generated by/at each target, and each of the one or more electrodes of the electrode array 110 may be used to detect the voltage signal generated by the target.

In an example, the electrode array 110 may include one or more reference electrodes.

The reference electrode of the electrode array 110 may detect or obtain a reference electrical signal of a target that is in contact with the reference electrode. In one example, the neural recording apparatus 100 may stimulate the target of the reference electrode by applying the electrical signal (e.g., the applied electrical signal) to the target of the reference electrode through the reference electrode of the electrode array 110. When the target of the reference electrode is stimulated by the applied electrical signal, a voltage signal may be generated, and the reference electrode may detect the voltage signal generated by the target. The electrical signal detected by the reference electrode may be referred to as a "reference signal," or "reference electrical signal."

Each of the electrodes of the electrode array 110 may transmit their detected (or obtained) electrical signal to the AFE circuit 120. The reference electrode of the electrode array 110 may transmit the detected reference electrical signal to the AFE circuit 120.

The AFE circuit 120 may generate a digital signal based on the electrical signals received from the electrodes of the electrode array 110 and the reference signal received from the reference electrode of the electrode array 110. For example, the AFE circuit 120 may regulate the reference signal and may generate current signals by performing transconductance based on the detected voltage signals and the regulated reference signal through transconductance circuits. In one example, the transconductance may include a conversion and an amplification from a voltage to a current. The AFE circuit 120 may perform multiplexing on the generated current signals through a multiplexer (MUX) and convert the multiplexed current signals into a digital signal through an analog-to-digital converter (ADC).

As will be described in detail below, as the AFE circuit 120 may process the multiplexed current signals with one ADC for generating the digital signal, the area per channel of the AFE circuit 120 may be small at the level of the electrode size of the electrode array 110. That is, an AFE channel may be secured in each pitch of the microelectrode. In addition, since the AFE circuit 120 may perform multiplexing after performing amplification through the transconductance circuits, a memory effect may be prevented and a crosstalk phenomenon may be reduced or eliminated.

The neural recording apparatus 100 may include the communication circuit (or a communication interface) 130. The communication circuit may communicate by wire or wirelessly (e.g., where the communication circuit 130 is representative of one or more transceivers). The communication circuit 130 may communicate with the AFE 120, for example, to provide generated digital signals to the processor and memory 155. Accordingly, the neural recording apparatus 100 may transmit the digital signal(s) generated by one or more of the AFE circuits 120 to the processor and memory 155, which may be an external terminal (e.g., a computing device), through the communication circuit 130. The external terminal may analyze the activity of many targets by processing the digital signal(s) received from the neural recording apparatus 100. For example, the external terminal may analyze and/or map biological neural activities and/or connections using the received digital signal(s).

For example, the AFE circuit 120, according to an example, may be applied to the neural recording and a technique using the MEA (e.g., a digital physiology technique, a drug screening technique, etc.).

Figure 2:
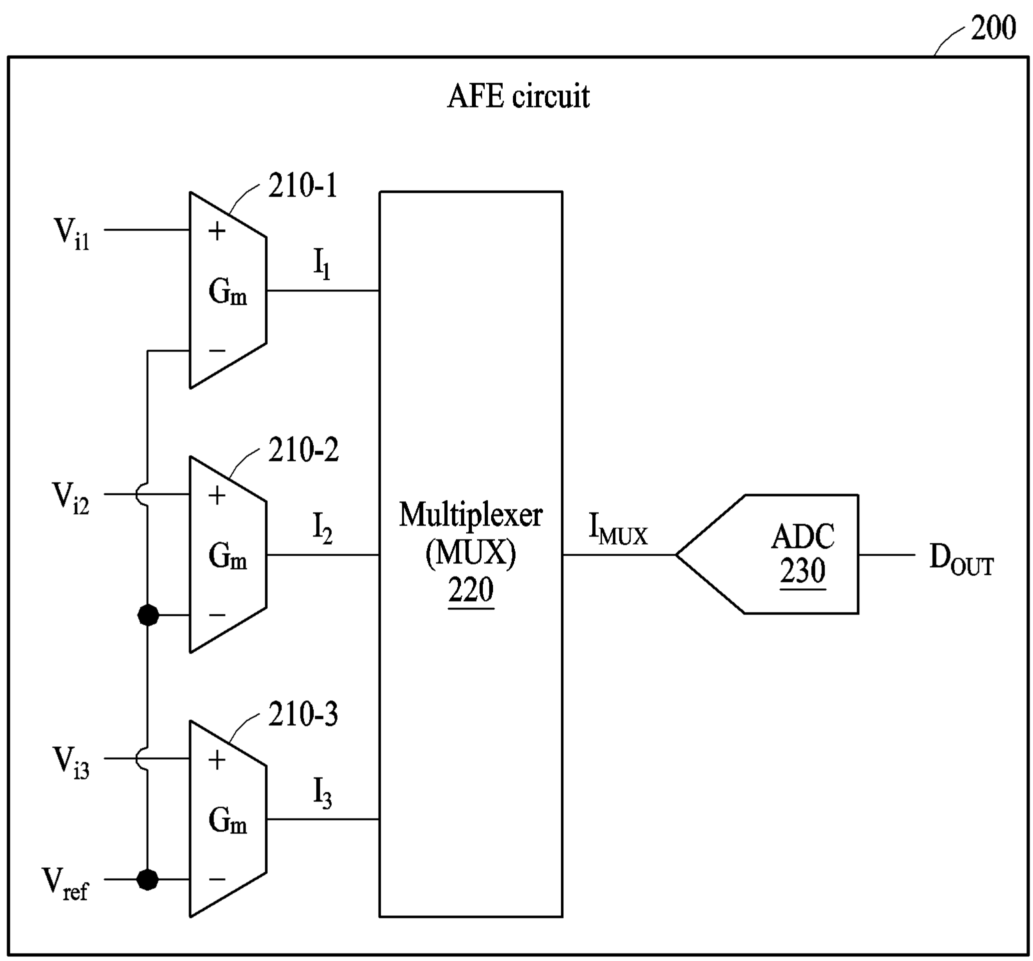
FIG. 2 illustrates an example of an analog front-end (AFE) circuit of a neural recording apparatus according to one or more embodiments.

FIG. 2 illustrates an example of an AFE circuit of a neural recording apparatus.

The AFE circuit 200 shown in FIG. 2 may correspond to the AFE circuit 120 of FIG. 1.

Referring to FIG. 2, the AFE circuit 200 may include a plurality of transconductance circuits 210-1 to 210-3, a MUX 220, and an ADC 230.

Although the AFE circuit 200 includes three transconductance circuits 210-1 to 210-3 in FIG. 2, this is merely an example, and the AFE circuit 200 may include three or more transconductance circuits.

In FIG. 2, each of $V_{i1}$, $V_{i2}$, and $V_{i3}$ may represent, for example, respective voltage signals detected by, and provided through, each of electrode$_1$, electrode$_2$, and electrode$_3$ of the electrode array 110, and $V_{ref}$ may represent a reference signal, such as discussed above.

The transconductance circuits 210-1 to 210-3 may generate respective current signal $I_1$, $I_2$, and $I_3$ by performing respective transconductance on a corresponding input voltage signal. As illustrated in the example of FIG. 2, the input signals include one or more input voltage signals $V_i$ and as well as a reference voltage signal $V_{ref}$. In addition, the transconductance circuits 210-1 to 210-3 may transmit each of their respective current signals to the MUX 220. For example, the transconductance circuit 210-1 may generate a current signal $I_1$ corresponding to Gm $(V_{i1}-V_{ref})$ from the input voltage signal $V_{i1}$ and $V_{ref}$. Here, Gm may represent a gain from an amplification or an amplifier. The transconductance circuit 210-1 may transmit the current signal $I_1$ to the MUX 220. The transconductance circuit 210-2 may generate a current signal $I_2$ corresponding to Gm $(V_{i2}-V_{ref})$ from the input voltage signal $V_{i2}$ and $V_{ref}$. The transconductance circuit 210-2 may transmit the current signal $I_2$ to the MUX 220. The transconductance circuit 210-3 may generate a current signal $I_3$ corresponding to Gm $(V_{i3}-V_{ref})$ from the input voltage signal $V_{i3}$ and $V_{ref}$. The transconductance circuit 210-3 may transmit the current signal $I_3$ to the MUX 220.

The MUX 220 may perform multiplexing on the input current signals $I_1$, $I_2$, and $I_3$. After performing the multiplexing on the input current signals, the MUX 220 may then transmit the multiplexed current signals $I_{MUX}$ to the ADC 230.

Referring to FIG. 2, the MUX 220 may perform multiplexing on the input current signals $I_1$, $I_2$, and $I_3$ in a time domain. That is, the MUX 220 may perform time division multiplexing (TDM) on the input current signals $I_1$, $I_2$, and $I_3$. For example, the MUX 220 may transmit the current signal $I_1$, the current signal $I_2$, and the current signal $I_3$ in an order of the current signal $I_1$, the current signal $I_2$, and the current signal $I_3$ to the ADC 230.

In an example, the MUX 220 may perform multiplexing on the input current signals $I_1$, $I_2$, and $I_3$ in a frequency domain. For example, the MUX 220 may modulate each of the current signals $I_1$, $I_2$, and $I_3$ into different frequencies, e.g., respective modulation frequency 1 (MOD1), modulation frequency 2 (MOD2), and modulation frequency 3 (MOD3) shown in FIG. 3. The MUX 220 may then transmit the modulated current signal $I_1$, the modulated current signal $I_2$, and the modulated current signal $I_3$ to the ADC 230.

The ADC 230 may convert the input current signal (e.g., the multiplexed current signals $I_{MUX}$) into a digital signal $D_{out}$.

A multi-channel may be formed (or included) in the neural recording apparatus 100. Here, each of the channels of the multi-channel may respectively include, for each of the electrodes, a corresponding transconductance circuit for a corresponding electrode of the electrodes, the MUX 220, and the ADC 230. In the example shown in FIG. 2, three channels may be formed. For example, a channel 1 may include an electrode$_1$ that detects $V_{i1}$, the corresponding transconductance circuit 210-1 of the electrode$_1$, the MUX 220, and the ADC 230. That is, the electrode$_1$, the corresponding transconductance circuit 210-1 of the electrode$_1$, the MUX 220, and the ADC 230 may form channel 1. Channel 2 may include an electrode$_2$ that detects $V_{i2}$, the corresponding transconductance circuit 210-2 of the electrode$_2$, the MUX 220, and the ADC 230. That is, the electrode$_2$ that measures $V_{i2}$, the corresponding transconductance circuit 210-2 of the electrode$_2$, the MUX 220, and the ADC 230 may form channel 2. Channel 3 may include an electrode$_3$ that measures $V_{i3}$, the corresponding transconductance circuit 210-3 of the electrode$_3$, the MUX 220, and the ADC 230. That is, the electrode 3 that measures $V_{i3}$, the corresponding transconductance circuit 210-3 of the electrode$_3$, the MUX 220, and the ADC 230 may form channel 3. Channel 1, channel 2, and channel 3 may share the MUX 220 and ADC 230.

In the example shown in FIG. 2, the AFE 200 may convert (or combine) the multi-channel signals $I_1$, $I_2$, and $I_3$ into the single signal $I_{MUX}$ through the MUX 220 and a single ADC, such as ADC 230, may be used to process a single signal. Accordingly, an area per channel of the AFE 200 (or the area per channel allocated to the ADC 230) may be reduced to the level of the electrode's size, and each corresponding circuitry of the AFE 200, for receiving a voltage measured from a corresponding electrode, may be disposed in a chip and/or attached to the electrode array 110 with a pitch matching the pitch of the electrodes of the electrode array 110. This pitch relationship between the AFE 200 and the electrode array 110 with respect to FIG. 2 is also applicable to the remaining examples.

The electrical signals detected by the electrodes of the electrode array 110 may have a very small amplitude (e.g., several tens to several hundred microvolt (μV)) and a high contact impedance (e.g., several tens to several hundreds of megohm MΩ). When the detected electrical signals are multiplexed and then amplified, a memory effect due to the contact impedance may occur, a crosstalk phenomenon may occur, and a signal-to-noise ratio (SNR) drop may occur.

Because the AFE 200 may perform multiplexing after amplifying through the transconductance circuits 210-1 to 210-3 such as those shown in the example of FIG. 2, the memory effect may not occur, the crosstalk phenomenon may be reduced or eliminated, and the SNR drop may be prevented.

Figure 3:
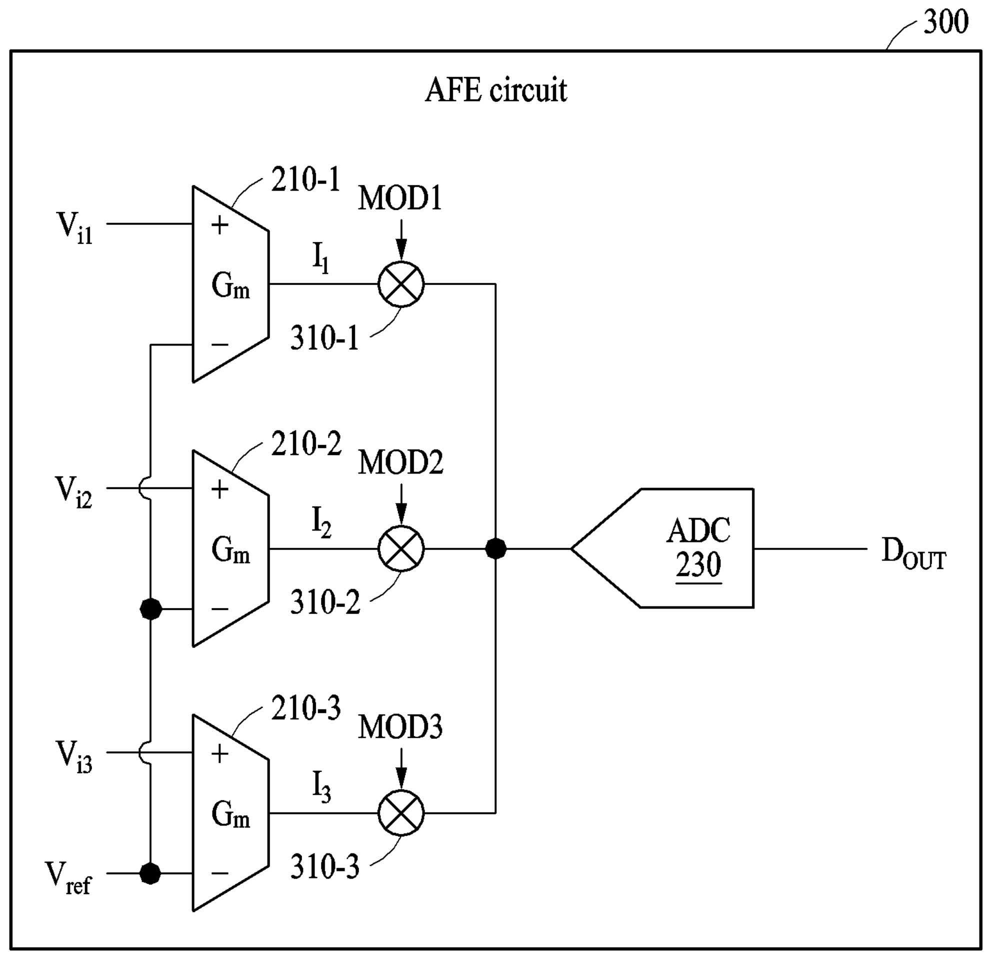
FIG. 3 illustrates an example of an AFE circuit of a neural recording apparatus according to one or more embodiments.

FIG. 3 illustrates an example of an AFE circuit of a neural recording apparatus.

Referring to FIG. 3, the AFE circuit 300 shown in FIG. 3 may correspond to the example of the AFE circuit 120 of FIG. 1. In addition, the AFE circuit 300 may include a plurality of transconductance circuits 210-1 to 210-3, a plurality of modulators 310-1 to 310-3, and the ADC 230.

The operation of the modulators 310-1 to 310-3 may correspond to the example of multiplexing in the frequency domain of the MUX 220 of FIG. 2.

Each of the modulators 310-1 to 310-3 may include, for example, a chopper, but is not limited thereto.

Each of the modulators 310-1 to 310-3 may respectively perform modulation (e.g., chopper modulation) on an input current signal and may transmit each of the modulated current signals to the ADC 230.

In the example shown in FIG. 3, similar to the AFE 200, the area per channel of the AFE 300 may be reduced to the level of the electrode size. In addition, similar to the AFE 200, since the AFE 300 may perform modulation after performing amplification through the transconductance circuits 210-1 to 210-3, the memory effect may not occur, the crosstalk phenomenon may be reduced or eliminated, and the SNR drop may not be prevented.

Figure 4:
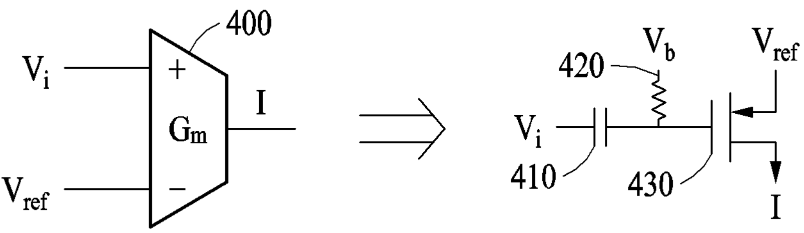
FIG. 4 illustrates an example of a transconductance circuit in an AFE circuit according to one or more embodiments.

FIG. 4 illustrates an example of a transconductance circuit 400 in an AFE circuit.

Referring to FIG. 4, a transconductance circuit 400 may include a capacitor 410, a bias resistance 420, and a transistor 430.

The transconductance circuit 400 of FIG. 4 may be any of, or each of, the transconductance circuits 210-1 to 210-3 described with reference to FIGS. 2 to 3. That is, a structure of each of the transconductance circuits 210-1 to 210-3 may be the same as that of the transconductance circuit 400.

In the example of FIG. 4, the transconductance circuit 400 outputs a current signal I based on the reference voltage $V_{ref}$ and the input voltage signal $V_i$ provided to the capacitor 410. The capacitor 410 may remove a direct current (DC) component of the input voltage signal $V_i$. For example, when an electrode is in contact with a neuron, a DC potential may occur between the electrode and the neuron. The voltage signal $V_i$ may include the DC potential and the capacitor 410 may remove the DC potential from the input voltage signal $V_i$.

The transistor 430 may perform transconductance. The bias resistance 420 may be connected to one end of the capacitor 410 and a gate of the transistor 430.

As discussed above, the capacitor 410 may remove the DC component from the input voltage signal $V_i$ and a bias signal $V_b$ may also be applied to the gate of the transistor 430. That is, the voltage signal (e.g., the voltage signal from which the DC component is removed) passing through the capacitor 410 and the bias signal $V_b$ may be applied as the gate voltage of the transistor 430. A reference signal $V_{ref}$ may be applied to the source of the transistor 430. When the gate voltage and the source voltage are applied, the transistor 400 may generate and output the current signal I corresponding to Gm $(V_i-V_{ref})$.

In one example, each respective transconductance circuit 400 of the electrode array may be separated by a pitch that matches the corresponding pitch between the respective electrodes. Each transconductance circuit 400 may be repeated for each electrode so respective input voltage signals $V_i$ of different electrodes are provided at different pitch positions that match the different pitch positions of the electrodes, while the same measured reference voltage $V_{ref}$ may be provided to each transconductance circuit 400.

An element performing transconductance may include an operational transconductance amplifier (OTA). The OTA may include a plurality of transistors (e.g., five or more transistors), and thus has a size larger than the transconductance circuit 400 of FIG. 4. When each of the transconductance circuits 210-1 to 210-3 described with reference to FIGS. 2 to 3 are provided with the structure of the transconductance circuit 400, the sizes of the AFE circuits 120, 200, and 300 may be further reduced than when each of the transconductance circuits 210-1 to 210-3 corresponds to the OTA.

Figure 5:
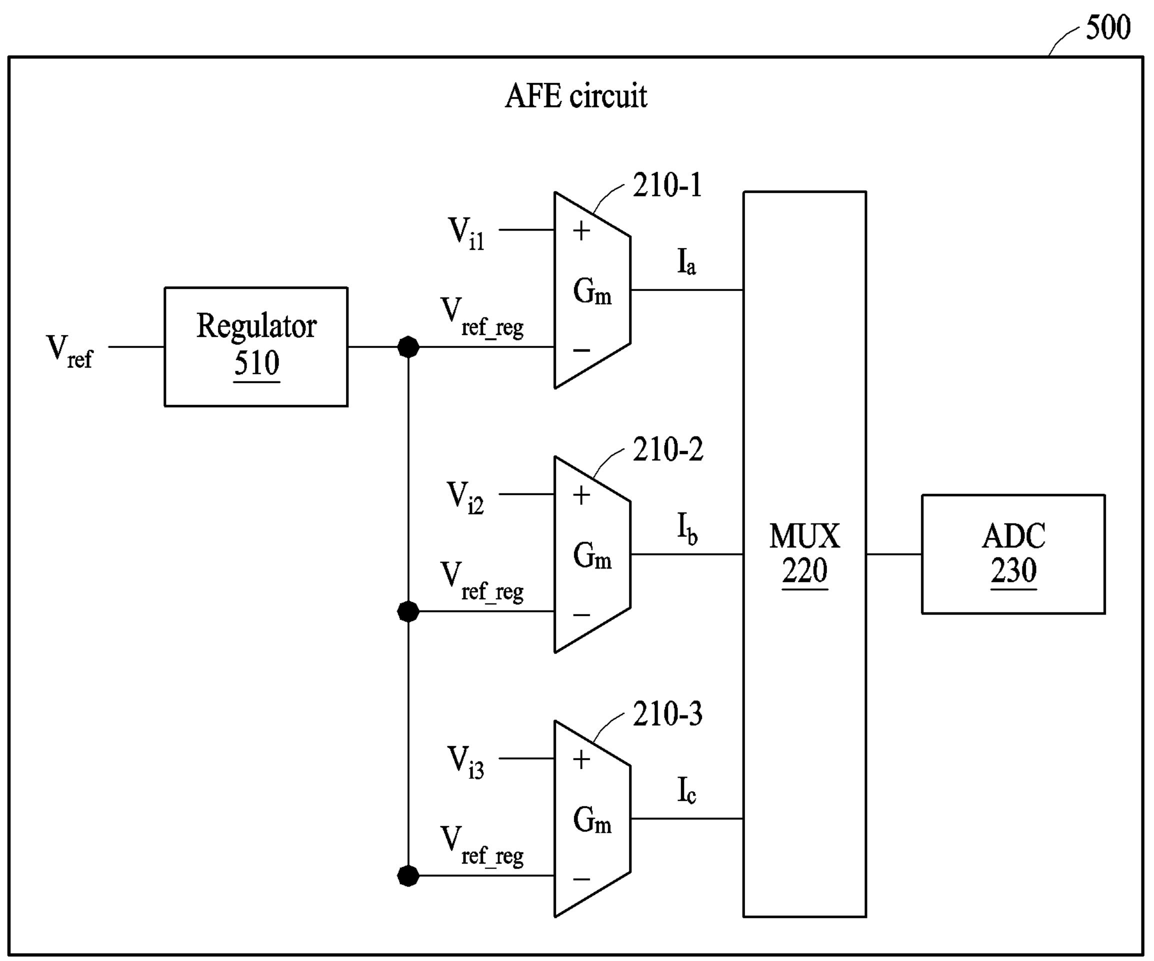
FIGS. 5 and 6 illustrate an example of an AFE circuit of a neural recording apparatus according to one or more embodiments.
Figure 6:
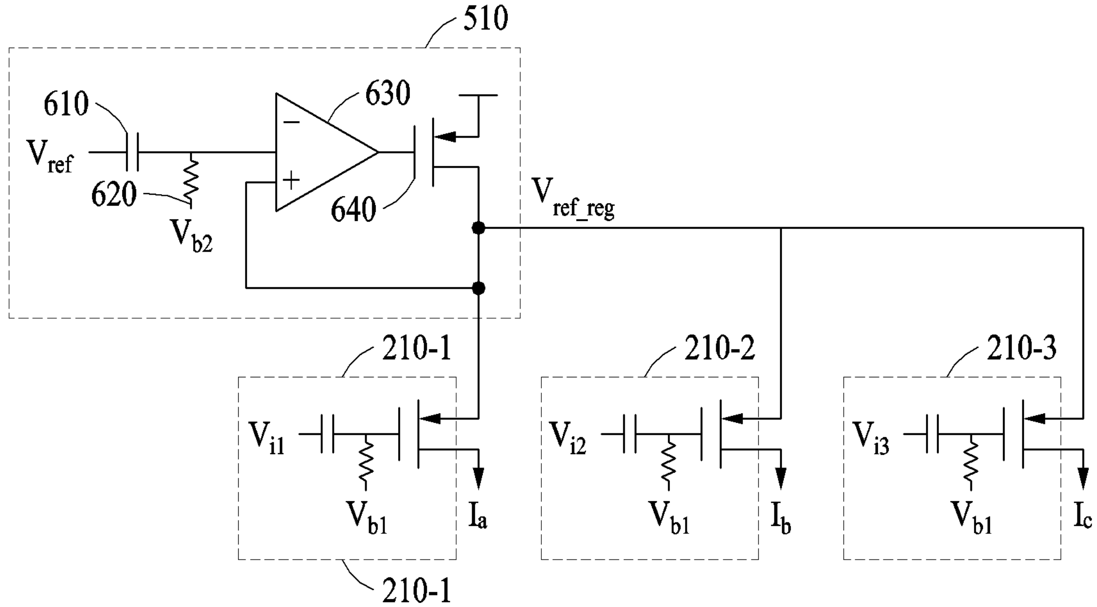

FIGS. 5 and 6 each illustrate examples of an AFE circuit of a neural recording apparatus.

Referring to FIG. 5, an AFE circuit 500 may correspond to the example of the AFE circuit 120 of FIG. 1.

Referring to FIG. 5, the AFE circuit 500 may include a regulator 510, the plurality of transconductance circuits 210-1 to 210-3, the MUX 220, and the ADC 230.

The regulator 510 may perform regulating (or boosting) on the reference signal $V_{ref}$ and may output (or provide) a regulated reference signal $V_{ref\_reg}$ to each of the transconductance circuits 210-1 to 210-3. As described with reference to FIG. 4, each of the transconductance circuits 210-1 to 210-3 may include a transistor. In some examples, the amplitude of the reference signal $V_{ref}$ may be too small to drive a source of the transistor of each of the transconductance circuits 210-1 to 210-3. The regulator 510 may regulate and boost a signal provided thereto to generate a boosted and regulated signal. Accordingly, in one or more examples, where the reference signal $V_{ref}$ is too small to drive a source of the transistor, the resulting boosted reference may be large enough to drive the source of the transistor. The regulator 510 may apply this regulated reference signal $V_{ref\_reg}$ (or the boosted reference signal) to a source of the transistor of each of the transconductance circuits 210-1 to 210-3.

Referring to FIG. 6, the regulator 510 may include a capacitor 610, a bias resistance 620, an operational amplifier (or a comparator) 630, and a transistor 640.

The capacitor 610 and the bias resistance 620 may be connected to a first terminal (− terminal) of the operational amplifier 630. An output signal of the transistor 640 may be fed back to a second terminal (+ terminal) of the operational amplifier 630.

An output terminal of the operational amplifier 630 may be connected to a gate of the transistor 640. A drain of the transistor 640 may be electrically connected to a source of the transistor of each of the transconductance circuits 210-1 to 210-3.

The transistor 640 may output the regulated reference signal $V_{ref\_reg}$, for example, when both an output signal of the operational amplifier 630 is applied as a gate voltage and a source voltage is applied.

A circuit configuration of the regulator 510 illustrated in FIG. 6 is merely an example, and the circuit configuration of the regulator 510 is not limited to the descriptions illustrated in FIG. 6.

The regulator 510 may apply the regulated reference signal $V_{ref\_reg}$ to a source of the transistor of each of the transconductance circuits 210-1 to 210-3. That is, each of the regulated reference signals $V_{ref\_reg}$ may be applied to the transistor of each of the transconductance circuits 210-1 to 210-3 to a source voltage.

Each of the transconductance circuits 210-1 to 210-3 may generate and output a current signal corresponding to Gm $(V_i-V_{ref\_reg})$. For example, the transconductance circuit 210-1 may generate a current signal 1, corresponding to Gm $(V_{i1}-V_{ref\_reg})$ and output it to the MUX 220, the transconductance circuit 210-2 may generate a current signal $I_b$ corresponding to Gm $(V_{i2}-V_{ref\_reg})$ and output it to the MUX 220, and the transconductance circuit 210-3 may generate a current signal corresponding to Gm $(V_{i3}-V_{ref\_reg})$ and output it to the MUX 220.

Again, in these examples, the MUX 220 may perform multiplexing on the input current signals $I_a$, $I_b$, and $I_c$ and may transmit the multiplexed current signals to the ADC 230. The ADC 230 may convert the multiplexed current signals into a digital signal.

Figure 7:
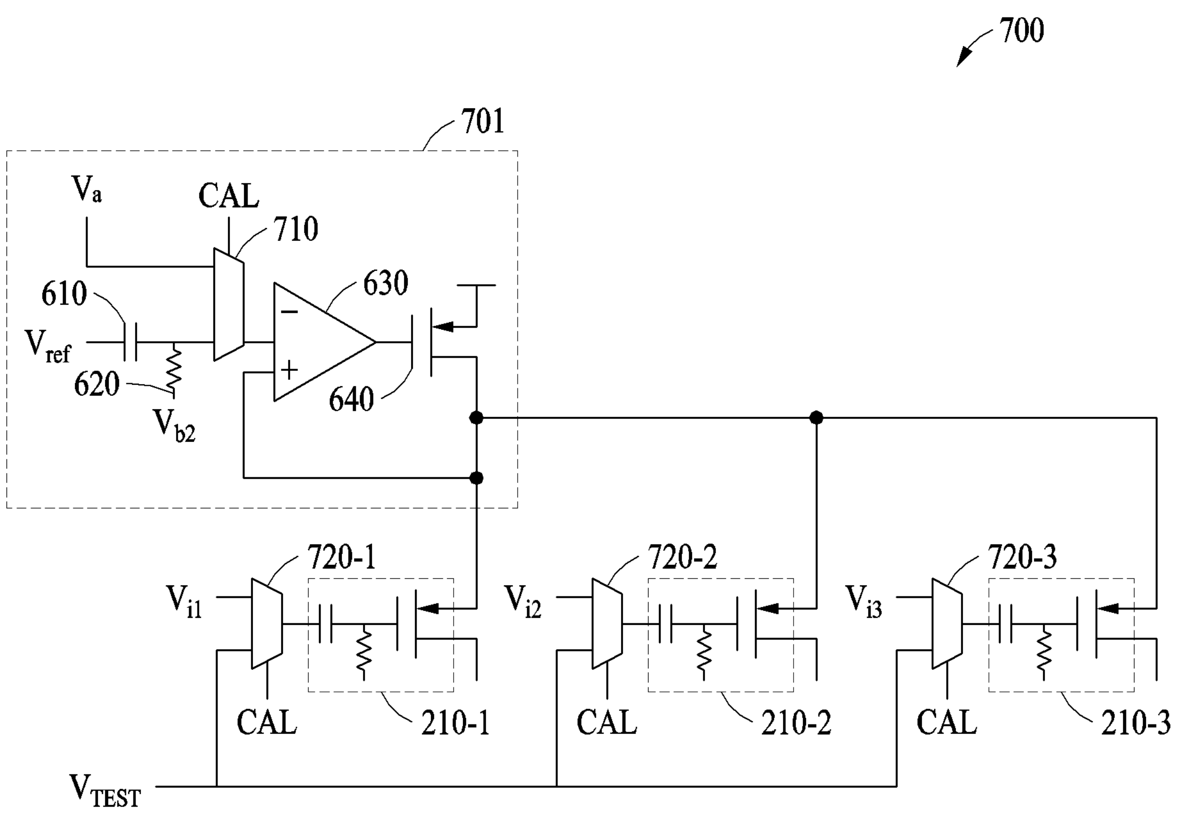
FIG. 7 illustrates an example of an AFE circuit of a neural recording apparatus according to one or more embodiments.

FIG. 7 illustrates an example of an AFE circuit 700 provided in of a neural recording apparatus.

Referring to FIG. 7, an AFE circuit 700 shown in FIG. 7 may correspond to the example of the AFE circuit 120 of FIG. 1.

The AFE circuit 700 may include a regulator 701, a plurality of MUXs 720-1 to 720-3, and the plurality of transconductance circuits 210-1 to 210-3. The MUX's illustrated in FIG. 7 may be a 2:1 MUX. For the sake of convenience, the MUX 220 and the ADC 230 illustrated, for example, in the AFE circuit 200 of FIG. 2 are omitted from FIG. 7 although the AFE circuit 700 may still include the MUX 220 and the ADC 230.

On the other hand, the regulator 701 may include a MUX 710. MUX 710 may be a 2:1 MUX. A first input terminal of the MUX 710 may be connected to a first voltage source to be described later and a second input terminal of the MUX 710 may be connected to the capacitor 610 and the bias resistance 620. An output terminal of the MUX 710 may be connected to an input terminal (e.g., a first terminal) of the operational amplifier 630.

Referring back to FIG. 1, the neural recording apparatus 100 may operate in a test mode and a measurement mode. The test mode may include performing a calibration (e.g., foreground calibration). The measurement mode may include obtaining or measuring a signal generated from a target.

The neural recording apparatus 100 may include a first voltage source that generates a first voltage signal $V_a$ when in the test mode while not generating the first voltage signal V a when in the measurement mode. The neural recording apparatus 100 may also include a second voltage source that generates a test voltage signal $V_{TEST}$ when in the test mode while not generating the test voltage signal $V_{TEST}$ when in the measurement mode.

The neural recording apparatus 100 may generate a calibration signal CAL in the test mode. Referring back to FIG. 7, the calibration signal CAL may be provided as a control signal to each of the MUXs 710 and 720-1 to 720-3.

When the CAL is input to the MUX 710 in the test mode, the MUX 710 may transmit the first voltage signal $V_a$ to the first terminal (– terminal) of the operational amplifier 630.

In the test mode, the regulator 701 may apply the regulated first voltage signal $V_{a\_reg}$ to the source of the transistor of each of the transconductance circuits 210-1 to 210-3.

When the CAL is input to each of the MUXs 720-1 to 720-3 in the test mode, each of the MUXs 720-1 to 720-3 may transmit the test voltage signal $V_{TEST}$ to each of the transconductance circuits 210-1 to 210-3.

Each of the transconductance circuits 210-1 to 210-3 may transmit, for example, a current signal corresponding to Gm ($V_{TEST}$–$V_{a\_reg}$) to the MUX 220. The MUX 220 may perform multiplexing on the input current signals and may transmit the multiplexed current signals to the ADC 230. The ADC 230 may convert the multiplexed current signals into a digital signal.

In the test mode, the neural recording apparatus 100 may transmit the digital signal to an external terminal through the communication interface. The external terminal may analyze the digital signal. For example, the external terminal may measure for a nonlinearity by processing the digital signal. In another example, the external terminal can perform a post-processing to the digital signal. The external terminal may transmit calibration information for calibrating the nonlinearity to the neural recording apparatus 100. The neural recording apparatus 100 may calibrate the nonlinearity based on the received calibration information.

When the test mode ends, the neural recording apparatus 100 may operate in the measurement mode. In the measurement mode, the neural recording apparatus 100 may not generate the CAL.

In the measurement mode, the MUX 710 may transmit the reference signal $V_{ref}$ to the first terminal of the operational amplifier 630. The regulator 701 may apply the regulated reference signal $V_{ref\_reg}$ to a source of the transistor of each of the plurality of transconductance circuits 210-1 to 210-3.

Each of the MUXs 720-1 to 720-3 may transmit a voltage signal measured by each of the electrodes to each of the transconductance circuits 210-1 to 210-3.

Each of the transconductance circuits 210-1 to 210-3 may then transmit a current signal corresponding to Gm ($V_i$–$V_{ref\_reg}$) to the MUX 220. The MUX 220 may then perform multiplexing on the input current signals and transmit the multiplexed current signals to the ADC 230. The ADC 230 may convert the multiplexed current signals into a digital signal.

When the nonlinearity is not calibrated in the test mode, a linearity drop by a 2nd harmonic may occur in the neural recording apparatus 100. When the nonlinearity is calibrated in the test mode, the linearity drop by the 2nd harmonic may be prevented from occurring in the neural recording apparatus 100.

Figure 8A:
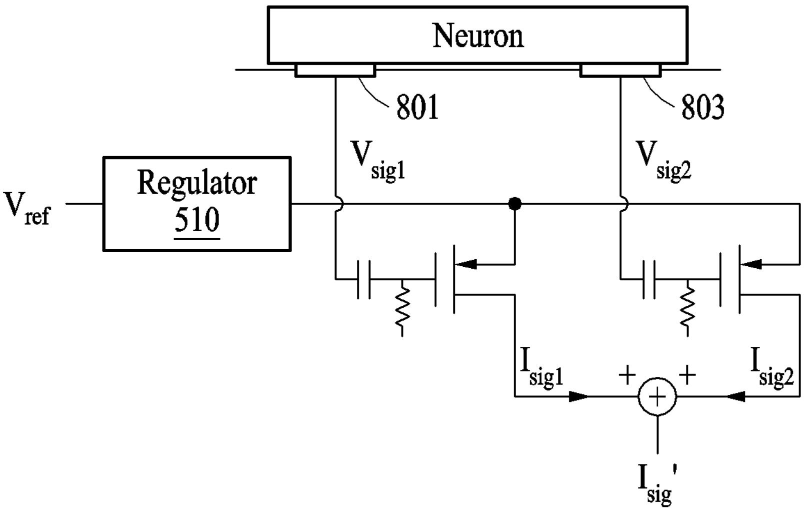
FIGS. 8A and 8B illustrate an example of merging current signals corresponding to the same neuron in an AFE circuit of a neural recording apparatus according to one or more embodiments.
Figure 8B:
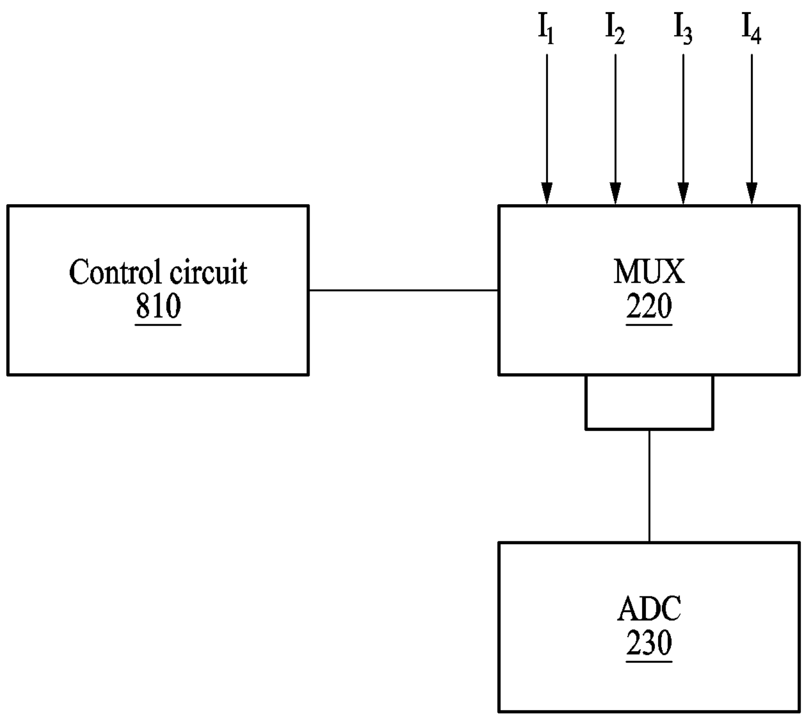

FIGS. 8A and 8B illustrate an example of merging current signals corresponding to the same neuron in an AFE circuit of a neural recording apparatus.

Referring to FIG. 8A, an example of merging of current signals corresponding to a same neuron is illustrated.

An electrode 801 and an electrode 803 may contact the same neuron. For example, the neuron may correspond to one of many neurons that are contacted by the electrodes of an electrode array, e.g., the electrode array 110 of FIG. 1. Electrode 801 may generate voltage signal $V_{sig1}$ from the neuron while electrode 803 may generate voltage signal $V_{sig2}$ from the neuron. In addition, as described above, a regulator such as the regulator 510 from FIG. 5 may be provided to provide a regulated reference signal.

The difference between the voltage signal $V_{sig1}$ detected by the electrode 801 and the regulated reference signal may be converted into a current signal $I_{sig1}$. The difference between the voltage signal $V_{sig2}$ detected by the electrode 803 and the regulated reference signal may be converted into a current signal $I_{sig2}$. The current signals $I_{sig1}$ and $I_{sig2}$ corresponding to the same neuron may be merged and transmitted to the ADC 230. That is, the current signals $I_{sig1}$ and $I_{sig2}$ of channels for the same neuron may be merged and transmitted to the ADC 230. The ADC 230 may convert the merged current signals (e.g., $I_{sig1}$+$I_{sig2}$) into a digital signal. The ADC 230 may reduce noise and improve the SNR by processing the merged current signals (e.g., $I_{sig1}$+$I_{sig2}$) rather than processing the current signal $I_{sig1}$ and the current signal $I_{sig2}$ separately.

In the example shown in FIG. 8B, the AFEs 120, 200, 300, 500, and 700 of FIGS. 1, 2, 3, 5, and 7 may include a control circuit 810 that merges current signals corresponding to the same neuron. The same label may be assigned to channels for the same neuron.

Referring to FIG. 8B, the control circuit 810 may be configured to know the label assigned to each of the channels. For example, the control circuit 810 may know that a label 1 is assigned to a channel corresponding to the current signal $I_1$ and a channel corresponding to the current signal $I_2$ and a label 2 is assigned to a channel corresponding to the current signal $I_3$ and a channel corresponding to the current signal $I_4$.

The control circuit 810 may be configured to control the MUX 220 to merge current signals of channels to which the same label is assigned. For example, when the current signals $I_1$, $I_2$, $I_3$, and $I_4$ are input to the MUX 220, the control circuit 810 may control the MUX 220 so that the current signal $I_1$ and the current signal $I_2$ are simultaneously output from the MUX 220. The current signal $I_3$ and the current signal $I_4$ may not be output from the MUX 220. As the current signal $I_1$ and the current signal $I_2$ are simultaneously output from the MUX 220, the current signal $I_1$ and the current signal $I_2$ may be merged, and the merged current signal $I_1$ and the merged current signal $I_2$ may be transmitted to the ADC 230. The control circuit 810 may be configured to control the MUX 220 so that the current signal $I_3$ and the current signal $I_4$ are simultaneously output from the MUX 220. As the current signal $I_3$ and the current signal $I_4$ are simultaneously output from the MUX 220, the current signal $I_3$ and the current signal $I_4$ may be merged, and the merged current signal $I_3$ and the merged current signal $I_4$ may be transmitted to the ADC 230.

In the example illustrated in FIG. 8B, the number of inputs and outputs of the MUX 220 is merely an example, and the number of inputs and outputs of the MUX 220 is not limited to the example illustrated in FIG. 8B.

Figure 9:
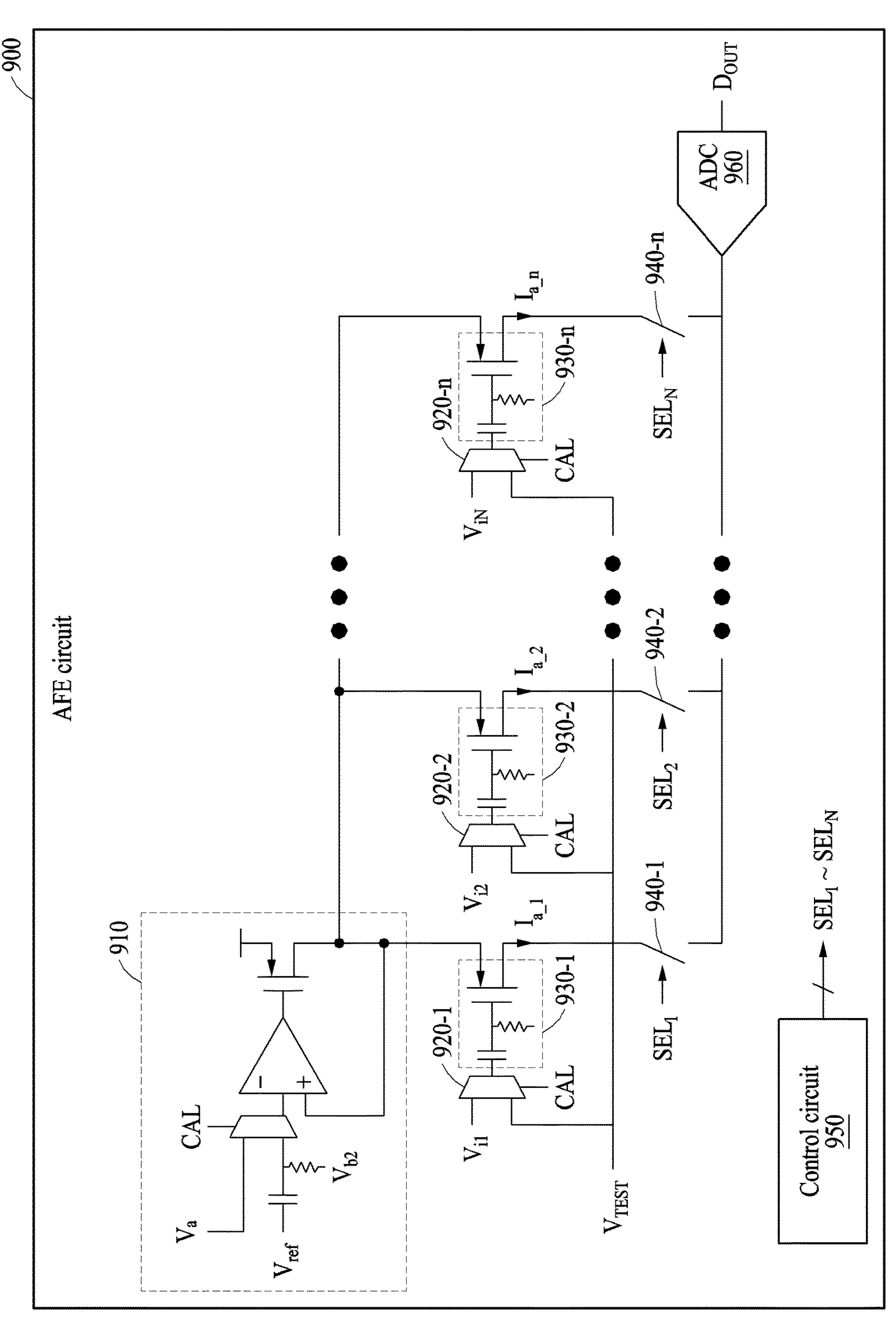
FIG. 9 illustrates an example of an AFE circuit of a neural recording apparatus according to one or more embodiments.

FIG. 9 illustrates an example of an AFE circuit 900 of a neural recording apparatus.

Referring to FIG. 9, an AFE circuit 900 shown in FIG. 9 may correspond to the example of the AFE circuit 120 of FIG. 1.

The AFE circuit 900 may include a regulator 910, a plurality of MUXs (e.g., 2:1 MUXs) 920-1 to **920-*n*, a plurality of transconductance circuits 930-1 to 930-*n*, a plurality of switches 940-1 to 940-*n*, a control circuit 950, and an ADC 960. According to an implementation, the control circuit 950 may be located outside the AFE circuit 900**.

The neural recording apparatus 100 including the AFE circuit 900 may operate in a test mode and a measurement mode. The test mode and the measurement mode may be comparable to the modes described with reference to FIG. 7.

Each of the MUXs 920-1 to **920-*n*** may transmit a test voltage signal $V_{TEST}$ to a corresponding transconductance circuit in the test mode and transmit a voltage signal detected by a corresponding electrode to a corresponding transconductance circuit in the measurement mode.

The descriptions of the MUXs 720-1 to **720-*n* of FIG. 7 may be applied to the descriptions of the MUXs 920-1 to 920-*n***.

Each of the transconductance circuits 930-1 to **930-*n* may correspond to the transconductance circuit 400 of FIG. 4. Each of the transconductance circuits 930-1 to 930-*n*** may include a transistor for performing transconductance, a capacitor connected to the transistor, and a bias resistance.

The regulator 910 may perform regulating the reference signal $V_{ref}$ and apply the regulated reference signal $V_{ref\_reg}$ as a source voltage of the transistor of each of the transconductance circuits 930-1 to **930-*n*. The description of the regulator 701 of FIG. 7 may be applied to the description of the regulator 910**.

Each of the transconductance circuits 930-1 to **930-*n* may perform transconductance on the input voltage signals (e.g., $V_i$ and $V_{ref\_reg}$) and may generate each of current signals (e.g., $I_{a\_1}$ to $I_{a\_n}$). The description of the transconductance circuits 210-1 to 210-3 described above may be applied to the description of the transconductance circuits 930-1 to 930-*n***.

The switches 940-1 to **940-*n* may be located between the transconductance circuits 930-1 to 930-*n* and the ADC 960**.

The control circuit 950 may be configured to turn on a switch of each of the transconductance circuits that generates current signals corresponding to the same neuron among the switches 940-1 to **940-*n* so that the current signals corresponding to the same neuron among the current signals (e.g., $I_{a\_1}$ to $I_{a\_n}$) are merged and input to the ADC 960. That is, the control circuit 950 may be configured to turn on a switch of each of the channels for the same neuron so that current signals of each of the channels for the same neuron are merged and input to the ADC 960. For example, the current signal $I_{a\_1}$ shown in FIG. 9 and a current signal $I_{a\_3}$ not shown in FIG. 9 may correspond to a first neuron. The control circuit 950 may be configured to turn on first switches (e.g., the switch 940-1 of the transconductance circuit 930-1 that generates the current signal $I_{a\_1}$ and the switch of the transconductance circuit that generates the current signal $I_{a\_3}$) to merge the current signals $I_{a\_1}$ and $I_{a\_3}$ of the channels for the first neuron. The control circuit 950 may be configured to turn off remaining switches except for the first switches. The current signal $I_{a\_2}$ and the current signal $I_{a\_n}$ illustrated in FIG. 9 may correspond to a second neuron. The control circuit 950 may be configured to turn on second switches (e.g., the switch 940-2 of the transconductance circuit 930-2 that generates the current signal $I_{a\_2}$ and the switch 940-*n* of the transconductance circuit 930-*n* that generates the current signal $I_{a\_n}$) to merge the current signals $I_{a\_2}$ and $I_{a\_n}$ of the channels for the second neuron. The control circuit 950 may be configured to turn off the remaining switches except for the second switches. In this way, the control circuit 950 may turn on the switch of each of the channels for the same neuron and turn off the remaining switches, so that the current signals corresponding to the same neuron may be merged and input to the ADC 960**.

The description provided with reference to FIGS. 1 to 8A and 8B may be applied to the description provided with reference to FIG. 9.

Figure 10:
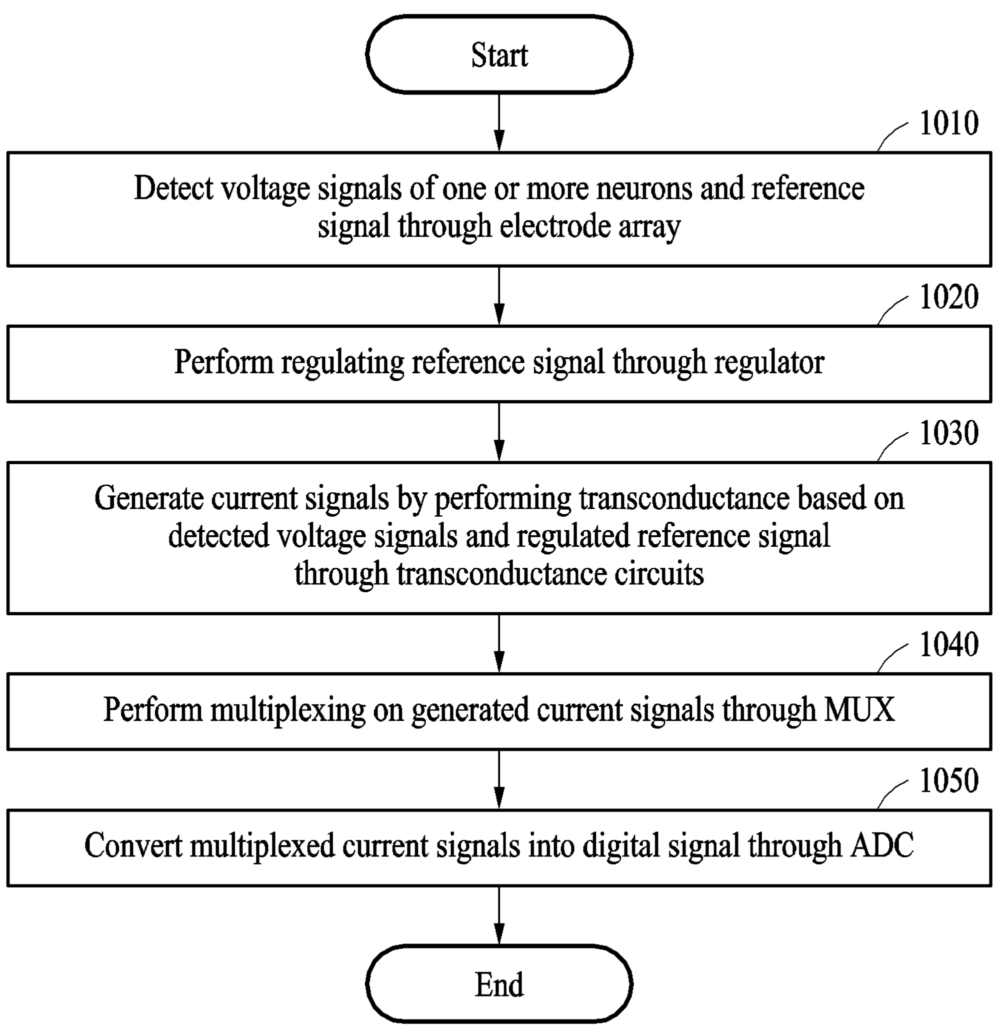
FIG. 10 illustrates an example of a method of operating a neural recording apparatus according to one or more embodiments.

FIG. 10 illustrates an example of a method of operating a neural recording apparatus.

Referring to FIG. 10, in operation 1010, the neural recording apparatus 100 may detect voltage signals of one or more neurons and a reference signal through the electrode array 110.

In operation 1020, the neural recording apparatus 100 may regulate the reference signal through the regulator.

In operation 1030, the neural recording apparatus 100 may generate current signals by performing a transconductance based on the detected voltage signals and the regulated reference signal through the transconductance circuits.

In operation 1040, the neural recording apparatus 100 may perform multiplexing on the generated current signals through the MUX.

In operation 1050, the neural recording apparatus 100 may convert the multiplexed current signals into a digital signal through the ADC.

In an example, the neural recording apparatus 100 may merge current signals corresponding to the same neuron among the generated current signals.

The description provided with reference to FIGS. 1 to 9 may be applied to the method of operating the neural recording apparatus 100 of FIG. 10.

The processors, memories, neural recording apparatuses 100, electrode arrays 110, communication circuits 130, AFE circuits 200, MUXs 220, ADCs 230, transconductance circuits 400, regulators 500, and other devices, and other components described herein are implemented as, and by, hardware components. Examples of hardware components that may be used to perform the operations described in this application where appropriate include controllers, sensors, generators, drivers, memories, comparators, arithmetic logic units, adders, subtractors, multipliers, dividers, integrators, and any other electronic components configured to perform the operations described in this application. In other examples, one or more of the hardware components that perform the operations described in this application are implemented by computing hardware, for example, by one or more processors or computers. A processor or computer may be implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices that is configured to respond to and execute instructions in a defined manner to achieve a desired result. In one example, a processor or computer includes, or is connected to, one or more memories storing instructions or software that are executed by the processor or computer. Hardware components implemented by a processor or computer may execute instructions or software, such as an operating system (OS) and one or more software applications that run on the OS, to perform the operations described in this application. The hardware components may also access, manipulate, process, create, and store data in response to execution of the instructions or software. For simplicity, the singular term "processor" or "computer" may be used in the description of the examples described in this application, but in other examples multiple processors or computers may be used, or a processor or computer may include multiple processing elements, or multiple types of processing elements, or both. For example, a single hardware component or two or more hardware components may be implemented by a single processor, or two or more processors, or a processor and a controller. One or more hardware components may be implemented by one or more processors, or a processor and a controller, and one or more other hardware components may be implemented by one or more other processors, or another processor and another controller. One or more processors, or a processor and a controller, may implement a single hardware component, or two or more hardware components. A hardware component may have any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods that perform the operations described in this application, and illustrated in FIGS. 1-10, are performed by computing hardware, for example, by one or more processors or computers, implemented as described above executing instructions or software to perform the operations described in this application that are performed by the methods. For example, a single operation or two or more operations may be performed by a single processor, or two or more processors, or a processor and a controller. One or more operations may be performed by one or more processors, or a processor and a controller, and one or more other operations may be performed by one or more other processors, or another processor and another controller, e.g., as respective operations of processor implemented methods. One or more processors, or a processor and a controller, may perform a single operation, or two or more operations.

Instructions or software to control computing hardware, for example, one or more processors or computers, to implement the hardware components and perform the methods as described above may be written as computer programs, code segments, instructions or any combination thereof, for individually or collectively instructing or configuring the one or more processors or computers to operate as a machine or special-purpose computer to perform the operations that be performed by the hardware components and the methods as described above. In one example, the instructions or software include machine code that is directly executed by the one or more processors or computers, such as machine code produced by a compiler. In another example, the instructions or software include higher-level code that is executed by the one or more processors or computers using an interpreter. The instructions or software may be written using any programming language based on the block diagrams and the flow charts illustrated in the drawings and the corresponding descriptions in the specification, which disclose algorithms for performing the operations that are performed by the hardware components and the methods as described above.

The instructions or software to control computing hardware, for example, one or more processors or computers, to implement the hardware components and perform the methods as described above, and any associated data, data files, and data structures, may be recorded, stored, or fixed in or on one or more non-transitory computer-readable storage media. Examples of a non-transitory computer-readable storage medium include read-only memory (ROM), random-access programmable read only memory (PROM), EEPROM, RAM, DRAM, SRAM, flash memory, non-volatile memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, blue-ray or optical disk storage, hard disk drive (HDD), solid state drive (SSD), flash memory, a card type memory such as multimedia card micro or a card (for example, secure digital (SD) or extreme digital (XD)), magnetic tapes, floppy disks, magneto-optical data storage devices, optical data storage devices, hard disks, solid-state disks, and any other device that is configured to store the instructions or software and any associated data, data files, and data structures in a non-transitory manner and provide the instructions or software and any associated data, data files, and data structures to one or more processors and computers so that the one or more processors and computers can execute the instructions. In one example, the instructions or software and any associated data, data files, and data structures are distributed over network-coupled computer systems so that the instructions and software and any associated data, data files, and data structures are stored, accessed, and executed in a distributed fashion by the one or more processors or computers.

While this disclosure includes specific examples, it will be apparent after an understanding of the disclosure of this application that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents.

What is claimed is:

1. A neural recording apparatus, the apparatus comprising:

an electrode array comprising:

a plurality of electrodes configured to respectively detect voltage signals of one or more neurons; and a reference electrode configured to detect a reference signal of a neuron;

a regulator configured to regulate the reference signal;

transconductance circuits configured to generate respective current signals by performing transconductance based on multiple voltage signals, of the detected voltage signals, and the regulated reference signal;

a first multiplexer (MUX) configured to multiplex the current signals; and an analog-to-digital converter (ADC) configured to convert the multiplexed current signals into a digital signal, wherein each of the transconductance circuits comprises:

a transistor configured to perform the transconductance; and a capacitor connected to the transistor, and wherein the regulator is configured to apply the regulated reference signal to the transistor of each of the transconductance circuits as a source voltage.

2. The apparatus of claim 1, wherein each of the transconductance circuits further comprises a bias resistance connected to a respective gate of the transistor of each of the transconductance circuits and to one end of the capacitor of each of the transconductance circuits.

3. The apparatus of claim 1, wherein each of the transconductance circuits is configured to receive each of the detected voltage signals, and wherein the capacitor of each of the transconductance circuits is configured to remove a direct current (DC) component of a respectively received voltage signal.

4. The apparatus of claim 3, wherein each of the voltage signals from which the DC component is removed and each of bias signals are configured to be applied as a gate voltage of the transistor of each of the transconductance circuits.

5. The apparatus of claim 1, further comprising a control circuit configured to merge current signals corresponding to a same neuron among the current signals.

6. The apparatus of claim 5, wherein the control circuit is configured to control the first MUX so that the current signals corresponding to the same neuron are simultaneously output from the first MUX.

7. The apparatus of claim 1, further comprising:

a first voltage source configured to generate a first voltage signal in a test mode for performing calibration and configured not to generate the first voltage signal in a measurement mode for detecting the voltage signals; and a second voltage source configured to generate a test voltage signal in the test mode and configured not to generate the test voltage signal in the measurement mode.

8. The apparatus of claim 7, wherein the regulator comprises:

an operational amplifier; and a second MUX connected to an input terminal of the operational amplifier, the second MUX being configured to transmit the first voltage signal to the operational amplifier in the test mode and configured to transmit the reference signal to the operational amplifier in the measurement mode, wherein each of the transconductance circuits further comprises a third MUX, the third MUX being configured to transmit the test voltage signal to the capacitor of each of the transconductance circuits in the test mode and configured to transmit each of the detected voltage signals to the capacitor of each of the transconductance circuits in the measurement mode.

9. The apparatus of claim 1, wherein the regulator, the plurality of transconductance circuits, the MUX, and the ADC comprise an analog front-end (AFE) circuit.

10. The apparatus of claim 1, further comprising a communication circuit configured to transmit the digital signal to an external device.

11. A neural recording apparatus, the apparatus comprising:

an electrode array comprising:

a plurality of electrodes configured to respectively detect voltage signals of one or more neurons; and a reference electrode configured to detect a reference signal of a neuron;

a regulator configured to regulate the reference signal;

transconductance circuits configured to generate current signals by performing transconductance based on multiple voltage signals, of the detected voltage signals, and the regulated reference signal;

an analog-to-digital converter (ADC);

a plurality of switches positioned between the transconductance circuits and the ADC; and a control circuit configured to turn on a switch of each of the transconductance circuits that generates the current signals corresponding to a same neuron among the plurality of switches so that current signals corresponding to the same neuron among the current signals are merged and input to the ADC, wherein each of the transconductance circuits comprises:

a transistor configured to perform the transconductance; and a capacitor connected to the transistor, and wherein the regulator is configured to apply the regulated reference signal to the transistor of each of the transconductance circuits as a source voltage.

12. The apparatus of claim 11, wherein the control circuit is configured to:

turn on first switches among the plurality of switches so that first current signals corresponding to a first neuron among the current signals are merged and input to the ADC while turning off second switches, the second switches comprising a first remaining portion of the plurality of switches excluding the first switches; and turn on third switches among the plurality of switches so that second current signals corresponding to a second neuron among the current signals are merged and input to the ADC while turning off fourth switches, the fourth switches comprising a second remaining portion of the plurality of switches excluding for the third switches.

13. The apparatus of claim 11, wherein each of the transconductance circuits further comprises a bias resistance connected to a respective gate of the transistor of each of the transconductance circuits and one end of the capacitor of each of the transconductance circuits.

14. The apparatus of claim 11, wherein each of the transconductance circuits is configured to receive each of the voltage signals, and wherein the capacitor of each of the transconductance circuits is configured to remove a direct current (DC) component of a respectively received voltage signal.

15. The apparatus of claim 14, wherein each of the voltage signals from which the DC component is removed and each of bias signals are configured to be applied as a gate voltage of the transistor of each of the transconductance circuits.

16. The apparatus of claim 11, further comprising:

a first voltage source configured to generate a first voltage signal in a test mode for performing calibration and configured not to generate the first voltage signal in a measurement mode for detecting the voltage signals; and a second voltage source configured to generate a test voltage signal in the test mode and configured not to generate the test voltage signal in the measurement mode.

17. The apparatus of claim 16, wherein the regulator comprises:

an operational amplifier; and a MUX connected to an input terminal of the operational amplifier and configured to transmit the first voltage signal to the operational amplifier in the test mode and configured to transmit the reference signal to the operational amplifier in the measurement mode, wherein each of the transconductance circuits further comprises a second MUX configured to transmit the test voltage signal to the capacitor of each of the transconductance circuits in the test mode and configured to transmit each of the voltage signals to the capacitor of each of the transconductance circuits in the measurement mode.

18. The apparatus of claim 11, wherein the regulator, the plurality of transconductance circuits, the ADC, the plurality of switches, and the control circuit comprise an analog front-end (AFE) circuit.

19. A method of operating a neural recording apparatus, the method comprising:

detecting voltage signals of one or more neurons and a reference signal of a neuron through an electrode array;

generating current signals by performing respective transconductances on the detected voltage signals, each transconductance being based on the reference signal;

performing multiplexing on the current signals through a multiplexer (MUX); and converting the multiplexed current signals into a digital signal through an analog-to-digital converter (ADC).

20. The method of claim 19, further comprising merging current signals corresponding to a same neuron among the generated current signals.

* * * * *